(12) United States Patent
Jonas et al.

(10) Patent No.: US 6,780,867 B2
(45) Date of Patent: Aug. 24, 2004

(54) THIENOPYRIMIDINES

(75) Inventors: Rochus Jonas, Darmstadt (DE); Hans-Michael Eggenweiler, Weiterstadt (DE); Pierre Schelling, Muehltal (DE); Maria Christadler, Roedermark (DE); Norbert Beier, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/362,993

(22) PCT Filed: Aug. 3, 2001

(86) PCT No.: PCT/EP01/08998
§ 371 (c)(1),
(2), (4) Date: Mar. 3, 2003

(87) PCT Pub. No.: WO02/18389
PCT Pub. Date: Mar. 7, 2002

(65) Prior Publication Data
US 2003/0187260 A1 Oct. 2, 2003

(30) Foreign Application Priority Data
Sep. 1, 2000 (DE) ......................... 100 42 997

(51) Int. Cl.$^7$ ................. A61K 31/519; C07D 495/04
(52) U.S. Cl. ................................. 514/267; 544/250
(58) Field of Search .................... 544/250; 514/267, 514/257

(56) References Cited

FOREIGN PATENT DOCUMENTS

| DE | 19752952 | * | 6/1998 |
| WO | WO 98/17668 | * | 4/1998 |

* cited by examiner

Primary Examiner—Richard L. Raymond
(74) Attorney, Agent, or Firm—Millen, White, Zelano, Branigan, P.C.

(57) ABSTRACT

Thienopyrimidines of the formula (I) and their physiologically acceptable salts, in which $R^1$, $R^2$ and X are as defined in claim 1, exhibit phosphodiesterase V inhibition and can be employed for the treatment of illnesses of the cardiovascular system and for the treatment and/or therapy of impotence.

20 Claims, No Drawings

THIENOPYRIMIDINES

The invention relates to compounds of the formula I

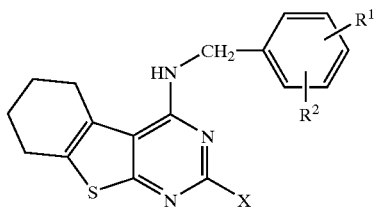

in which

R¹ and R² are each, independently of one another, H, A, OH, OA, NO₂ or Hal,

R¹ and R² together are alternatively alkylene having 3–5 carbon atoms, —O—CH₂—CH₂—, —CH₂—O—CH₂—, —O—CH₂—O— or —O—CH₂—CH₂—O—, X is mono-R⁵-substituted R³ or R⁴, R³ is linear or branched alkylene having 1–10 carbon atoms, in which one or two CH₂ groups may be replaced by —CH=CH— groups, O, NH or NA, R⁴ is cycloalkyl or cycloalkylalkylene having 5–12 carbon atoms, R⁵ is O(CH₂)ₙCOOH, O(CH₂)ₙCOOA, O(CH₂)ₙCONH₂, O(CH₂)ₙCONHA, O(CH₂)ₙCONA₂ or O(CH₂)ₙCN, S(O)ₘ(CH₂)ₙCOOH, S(O)ₘ(CH₂)ₙCOOA, S(O)ₘ(CH₂)ₙCONH₂, S(O)ₘ(CH₂)ₙCONHA, S(O)ₘ(CH₂)ₙCONA₂ or S(O)ₘ(CH₂)ₙCN, m is 0, 1 or 2, n is 1 or 2, A is alkyl having 1 to 6 carbon atoms, and Hal is F, Cl, Br or I, and their physiologically acceptable salts and/or solvates.

Pyrimidine derivatives are disclosed, for example, in WO 99/55708, EP 934321, EP 201 188 or WO 93/06104.

The invention had the object of finding novel compounds having valuable properties, in particular those which can used for the preparation of medicaments.

It has been found that the compounds of the formula I and their salts and/or solvates have very valuable pharmacological properties and are well tolerated.

In particular, they exhibit specific inhibition of cGMP phosphodiesterase (PDE V).

Quinazolines having a cGMP phosphodiesterase-inhibiting activity are described, for example, in J. Med. Chem. 36, 3765 (1993) and ibid. 37, 2106(1994).

The biological activity of the compounds of the formula I can be determined by methods as described, for example, in WO 93/06104. The affinity of the compounds according to the invention for cGMP and cAMP phosphodiesterase is determined by measuring their IC₅₀ values (concentration of the inhibitor needed to achieve 50% inhibition of the enzyme activity).

The determinations can be carried out using enzymes isolated by known methods (for example W. J. Thompson et al., Biochem. 1971, 10, 311). The experiment can be carried out using a modified batch method of W. J. Thompson and M. M. Appleman (Biochem. 1979, 18, 5228).

The compounds are therefore suitable for the treatment of illnesses of the cardiovascular system, in particular cardiac insufficiency, and for the treatment and/or therapy of impotence (erectile dysfunction).

The compounds are furthermore suitable for the treatment of angina, high blood pressure, high pulmonary pressure, congestive heart failure, atherosclerosis, conditions involving reduced passage through heart vessels, peripheral vascular diseases, strokes, bronchitis, allergic asthma, chronic asthma, allergic rhinitis, glaucoma, irritable bowel syndrome, tumours, renal insufficiency, liver cirrhosis and for the treatment of female sexual disorders.

The use of substituted pyrazolopyrimidinones for the treatment of impotence is described, for example, in WO 94/28902.

The compounds are effective as inhibitors of phenylephrine-induced contractions in corpus cavernosum preparations of rabbits. This biological action can be demonstrated, for example, by the method described by F. Holmquist et al. in J. Urol., 150, 1310–1315 (1993).

The inhibition of the contraction demonstrates the effectiveness of the compounds according to the invention for the therapy and/or treatment of impotence.

The compounds of the formula I can be employed as medicament active ingredients in human and veterinary medicine. They can furthermore be employed as intermediates for the preparation of further medicament active ingredients.

The invention accordingly relates to the compounds of the formula I and to a process for the preparation of compounds of the formula I according to Claim 1 and their salts, characterised in that a) a compound of the formula II

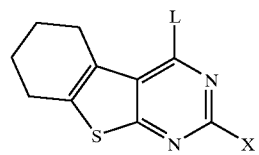

in which

X is as defined above, and L is Cl, Br, OH, SCH₃ or a reactive esterified OH group, is reacted with a compound of the formula III

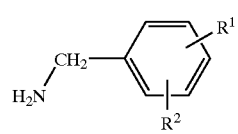

in which

R¹ and R² are as defined above, or b) a radical X in a compound of the formula I is converted into another radical X by, for example, hydrolysing an ester group to a COOH group or converting a COOH group into an amide or into a cyano group, and/or in that a compound of the formula I is converted into one of its salts.

Above and below, the radicals R¹, R², R³, R⁴, R⁵, X and L are as defined under the formulae I, II and III, unless expressly stated otherwise.

A is alkyl having 1–6 carbon atoms.

In the above formulae, alkyl is preferably unbranched and has 1, 2, 3, 4, 5 or 6 carbon atoms and is preferably methyl, ethyl or propyl, furthermore preferably isopropyl, butyl, isobutyl, sec-butyl or tert-butyl, but also n-pentyl, neopentyl, isopentyl or hexyl.

A is furthermore alkenyl having 2–6 carbon atoms, for example vinyl or propenyl.

A is furthermore a halogenated alkyl radical, such as, for example, trifluoromethyl.

X is a mono-$R^5$-substituted $R^3$ or $R^4$ radical.

$R^3$ is a linear or branched alkylene radical having 1–10 carbon atoms, where the alkylene radical is preferably, for example, methylene, ethylene, propylene, isopropylene, butylene, isobutylene, sec-butylene, pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, linear or branched heptylene, octylene, nonylene or decylene. $R^3$ is furthermore, for example, but-2-enylene or hex-3-enylene Very particular preference is given to methylene, ethylene, propylene or butylene.

$R^4$ is cycloalkylalkylene having 5–12 carbon atoms, preferably, for example, cyclopentylmethylene, cyclohexylmethylene, cyclohexylethylene, cyclohexylpropylene or cyclohexylbutylene. $R^4$ is alternatively cycloalkyl, preferably having 5–7 carbon atoms. Cycloalkyl is, for example, cyclopentyl, cyclohexyl or cycloheptyl.

$R^5$ is preferably, for example, $OCH_2COOH$, $OCH_2COOA$, $S(O)_mCH_2COOH$ or $S(O)_mCH_2COOA$.

Hal is preferably F, Cl or Br, but also I.

The radicals $R^1$ and $R^2$ may be identical or different and are preferably located in the 3- or 4-position of the phenyl ring. They are, for example, in each case independently of one another, H, OH, alkyl, F, Cl, Br or I or together are alkylene, such as, for example, propylene, butylene or pentylene, furthermore ethyleneoxy, methylenedioxy or ethylenedioxy. They are preferably also in each case alkoxy, such as, for example, methoxy, ethoxy or propoxy.

The term solvates is taken to mean hydrates or, for example, alcoholates.

For the entire invention, all radicals which occur more than once may be identical or different, i.e. are independent of one another.

Accordingly, the invention relates in particular to the compounds of the formula I in which at least one of the said radicals has one of the preferred meanings indicated above, Some preferred groups of compounds may be expressed by the following sub-formulae la to lf, which conform to the formula I and in which the radicals not designated in greater detail are as defined under the formula I, but in which in Ia X is $R^3$ which is substituted by $O(CH_2)_nCOOH$, $O(CH_2)_nCOOA$, $O(CH_2)_nCONH_2$, $O(CH_2)_nCONHA$, $O(CH_2)_nCONA_2$ or $O(CH_2)_nCN$, $S(O)_m(CH_2)_nCOOH$, $S(O)_m(CH_2)_nCOOA$, $S(O)_m(CH_2)_nCONH_2$, $S(O)_m(CH_2)_nCONHA$, $S(O)_m(CH_2)_nCONA_2$ or $S(O)_m(CH_2)_nCN$;

in Ib $R^1$ and $R^2$ are each, independently of one another, Hal, OH or OA,

X is $R^3$ which is substituted by $O(CH_2)_nCOOH$, $O(CH_2)_nCOOA$, $S(O)_m(CH_2)_nCOOH$ or $S(O)_m(CH_2)_nCOOA$;

in Ic $R^1$ and $R^2$ are each, independently of one another, Hal, OH or OA,

X is $R^3$ which is substituted by $O(CH_2)_nCOOH$, $O(CH_2)_nCOOA$, $S(O)_m(CH_2)_nCOOH$ or $S(O)_m(CH_2)_nCOOA$, $R^3$ is methylene, ethylene or propylene;

in Id $R^1$ and $R^2$ are each, independently of one another, Hal, OH or OA, $R^1$ and $R^2$ together are alkylene having 3–5 carbon atoms, —O—CH$_2$—CH$_2$—, —O—CH$_2$—O— or —O—CH$_2$—CH$_2$—O, X is $R^3$ which is substituted by $O(CH_2)_nCOOH$, $O(CH_2)_nCOOA$, $S(O)_m(CH_2)_nCOOH$ or $S(O)_m(CH_2)_nCOOA$, $R^3$ is methylene, ethylene or propylene;

in Ie $R^1$ and $R^2$ are each, independently of one another, H, Hal, A, $NO_2$, OH or OA, $R^1$ and $R^2$ together are alkylene having 3–5 carbon atoms, —O—CH$_2$—CH$_2$—, —O—CH$_2$—O— or —O—CH$_2$—CH$_2$—O, X is $R^3$ which is substituted by $O(CH_2)_nCOOH$, $O(CH_2)_nCOOA$, $S(O)_m(CH_2)_nCOOH$ or $S(O)_m(CH_2)_nCOOA$, $R^3$ is methylene, ethylene or propylene, A is alkyl having 1–6 carbon atoms or $CF_3$;

in If $R^1$ and $R^2$ are each, independently of one another, H, Hal, A, $NO_2$, OH or OA, $R^1$ and $R^2$ together are —O—CH$_2$—O— or —O—CH$_2$—CH$_2$—O—, X is $R^3$ which is substituted by $O(CH_2)_nCOOH$, $O(CH_2)_nCOOA$, $S(O)_m(CH_2)_nCOOH$ or $S(O)_m(CH_2)_nCOOA$, $R^3$ is methylene, ethylene or propylene, A is alkyl having 1–6 carbon atoms or $CF_3$;

and their physiologically acceptable salts and/or solvates.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

In the compounds of the formulae II or III, $R^1$, $R^2$ and X have the meanings indicated, in particular the preferred meanings indicated.

If L is a reactive esterified OH group, this is preferably alkylsulfonyloxy having 1–6 carbon atoms (preferably methylsulfonyloxy) or arylsulfonyloxy having 6–10 carbon atoms (preferably phenyl- or p-tolylsulfonyloxy, furthermore also 2-naphthalenesulfonyloxy).

The compounds of the formula I can preferably be obtained by reacting compounds of the formula II with compounds of the formula III.

If desired, the starting materials can also be formed in situ by not isolating them from the reaction mixture, but instead immediately converting them further into the compounds of the Formula I.

On the other hand, it is possible to carry out the reaction stepwise.

The starting compounds of the formula II and III are generally known. If they are not known, they can be prepared by methods known per se. Compounds of the formula II can be obtained, for example, from the corresponding hydroxypyrimidines, which are built up from thiophene derivatives and CN-substituted alkylenecarboxylic acid esters (Eur. J. Med. Chem. 23, 453 (1988)), by reaction with $POCl_3$.

The hydroxypyrimidinesare prepared either by dehydrogenation of corresponding tetrahydrobenzothienopyrimidine compounds or by the cyclisation of 2-aminobenzothiophene-3-carboxylic acid derivatives using aldehydes or nitriles, which is conventional for the preparation of pyrimidine derivatives (for example Houben-Weyl E9b/2).

In detail, the reaction of the compounds of the formula II with the compounds of the formula III is carried out in the presence or absence of an inert solvent at temperatures between about −20 and about 150°, preferably between 20 and 100°.

The addition of an acid-binding agent, for example an alkali or alkaline earth metal hydroxide, carbonate or bicarbonate or another salt of a weak acid of the alkali or alkaline earth metals, preferably of potassium, sodium or calcium, or the addition of an organic base, such as triethylamine, dimethylamine, pyridine or quinoline or of an excess of the amine component, may be favourable.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone or dimethylformamide (DMF); nitrites, such as acetonitrile; sulfoxides, such as dimethyl sulfoxide (DMSO); nitro compounds, such as nitromethane or nitrobenzene; esters, such as ethyl acetate, or mixtures of the said solvents.

It is furthermore possible to convert a radical X in a compound of the formula I into another radical X, for example by hydrolysing an ester or a cyano group to give a COOH group.

Ester groups can be saponified, for example, using NaOH or KOH in water, water/THF or water/dioxane at temperatures between 0 and 100°. Carboxylic acids can be converted into the corresponding carboxylic acid chlorides, for example using thionyl chloride, and these can be converted into carboxamides. Elimination of water therefrom in a known manner gives carbonitriles.

An acid of the formula I can be converted into the associated acid-addition salt using a base, for example by reaction of equivalent amounts of the acid and the base in an inert solvent, such as ethanol, followed by evaporation. Suitable bases for this reaction are, in particular, those which give physiologically acceptable salts.

Thus, the acid of the formula I can be converted into the, corresponding metal salt, in particular alkali metal or alkaline earth metal salt, or into the corresponding ammonium salt using a base (for example sodium hydroxide, potassium hydroxide, sodium carbonate or potassium carbonate). Also suitable for this reaction are, in particular, organic bases which give physiologically acceptable salts, such as, for example, ethanolamine.

On the other hand, a base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable acids. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid. Salts with physiologically unacceptable acids, for example picrates, can be used for the isolation and/or purificatior of the compounds of the formula I.

The invention furthermore relates to the use of the compounds of the formula I and/or their physiologically acceptable salts for the production of pharmaceutical preparations, in particular by non-chemical methods. They can be converted into a suitable dosage form here together with at least one solid, liquid and/or semiliquid excipient or assistant and optionally in combination with one or more further active ingredients.

The invention also relates to medicaments of the formula I and their physiologically acceptable salts as phosphodiesterase V inhibitors.

The invention furthermore relates to pharmaceutical preparations comprising at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical administration and do no react with the novel compounds, for example water, vegetable oils, benzyl alcohols, alkylene glycols, polyethylene glycols, glycerol triacetate, gelatine, carbohydrates, such as lactose or starch, magnesium stearates, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, colorants and flavours and/or a plurality of further active ingredients, for example one or more vitamins.

The compounds of the formula I and their physiologically acceptable salts can be employed for combating illnesses in which an increase in the cGMP (cycloguanosine monophosphate) level results in inflammation inhibition or prevention and muscle relaxation. The compounds according to the invention are used in particular in the treatment of illnesses of the cardiovascular system and for the treatment and/or therapy of impotence.

The invention relates to the use of the compounds of the formula I and their physiologically acceptable salts and/or solvates for the preparation of a medicament for the treatment of angina, high blood pressure, high pulmonary pressure, congestive heart failure, atherosclerosis, conditions involving reduced passage through heart vessels, peripheral vascular diseases, strokes, bronchitis, allergic asthma, chronic asthma, allergic rhinitis, glaucoma, irritable bowel syndrome, tumours, renal insufficiency, liver cirrhosis and for the treatment of female sexual disorders.

In general, the substances are preferably administered in doses of between about 1 and 500 mg, in particular between 5 and 100 mg per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular illness to which the therapy applies. Oral administration is preferred.

Above and below, all temperatures are given in ° C. In the examples below, "conventional work-up" means that water is added if necessary, a pH of from 2 to 10, depending on the constitution of the end product, is set if necessary, the mixture is extracted with ethyl acetate or dichloromethane, the phases are separated, the organic phase is dried over sodium sulfate and evaporated, and the product is purified by chromatography on silica gel and/or by crystallisation.

Mass spectrometry (MS): EI (electron impact ionisation) $M^+$ FAB (fast atom bombardment) $(M+H)^+$

EXAMPLE 1

357 ml of cyclohexanone are added dropwise at room temperature to a suspension of 115 g of sulfur and 300 ml of methyl cyanoacetate in 500 ml of methanol. 350 ml of diethylamine are then slowly added, during which the temperature is held at a maximum of 50°. The mixture is stirred for a further 12 hours and cooled to 4°, and the crystals are separated off and washed with ice-cold methanol. Drying gives 580 g of methyl 2-amino-4,5,6,7tetrhydrobenzo[b]thiophene-3-carboxylate ("AA"), m.p. 130°.

40 ml of chloroacetonitrile are added to a solution of 106 g of "AA" in 600 ml of dioxane, and HCl is passed in at 40–500° for 3 hours with stirring. The mixture is stirred for a further 2 hours, the solvent is removed, and the mixture is subjected to conventional work-up, giving 125 g of 2-chloromethyl-5,6,7,8-tetrahydro-3H-benzo[4,5]thieno[2,3-d]pyrimidin-4-one ("AB"), m.p. 285–286°.

1.7 g of sodium hydride (50% suspension) are added to a solution of 5.0 g of "AB" and 2.8 g of butyl glycolate in 100 ml of THF, and the mixture is refluxed for 3 hours. The solvent is removed, and the mixture is subjected to conventional work-up, giving 5.0 g of butyl (4-oxo-3,4,5,6,7,8-hexahydrobenzo[4,5]thieno[2,3-d]pyrimidin-2-ylmethoxy)acetate ("AC"). 1 ml of DMF is added to a solution of 5.0 g of "AC" in 50 ml of thionyl chloride, and the mixture is stirred at 45° for 2 hours. After the solvent has been removed, the mixture is subjected to conventional work-up, giving 4.5 g of butyl (4-chloro-5,6,7,8-tetrahydrobenzo[4,5]thieno[2,3-d]pyrimidin-2-ylmethoxy)acetate ("AD").

EXAMPLE 2

The compound butyl (4-chloro-5,6,7,8-tetrahydrobenzo[4,5]thieno[2,3-d]-pyrimidin-2-ylethoxy)acetate ("AE") is obtained analogously by reaction of "AA" with chloropropionitrile and further reaction analogously to Example 1.

EXAMPLE 3

A solution of 4.5 g of "AD" and 4.5 g of 3-chloro-4-methoxybenzylamine in 30 ml of 1-methylpyrrolidone is heated at 100° for 1 hour. The solvent is removed, and the mixture is subjected to conventional work-up, giving 1.8 g of butyl [4-(3-chloro-4-methoxybenzylamino)-5,6,7,8-tetrahydrobenzo[4,5]thieno[2,3-d]pyrimidin-2-ylethoxy]acetate.

The compound butyl [4-(3-chloro-4-methoxybenzylamino)-5,6,7,8-tetrahydrobenzo[4,5]thieno[2,3-d]pyrimidin-2-ylethoxy]acetate is obtained analogously from "AE".

Analogous reaction of 3,4-methylenedioxybenzylamine,
3,4-dimethoxybenzylamine,
4-methoxybenzylamine,
3,4-dichlorobenzylamine,
4-chlorobenzylamine,
4-methylbenzylamine,
4-fluorobenzylamine,
benzylamine,
3-chloro-4-nitrobenzylamine,
2,4-dichlorobenzylamine,
2-chloro-4-fluorobenzylamine,
3-fluorobenzylamine,
2-methoxybenzylamine,
2-chlorobenzylamine,
3,5-di(trifluoromethoxy)benzylamine, with "AD" or "AE" gives the following compounds butyl [4-(3,4-methylenedioxybenzylamino)-5,6,7,8-tetrahydrobenzo-[4,5]thieno[2,3-d]pyrimidin-2-ylmethoxy]acetate, butyl [4-(3,4-dimethoxybenzylamino)-5,6,7,8-tetrahydrobenzo[4,5]-thieno[2,3-d]pyrimidin-2-ylmethoxy]acetate, butyl [4-(4-methoxybenzylamino)-5,6,7,8-tetrahydrobenzo[4,5]thieno-[2,3-d]pyrimidin-2-ylmethoxy]acetate, butyl [4-(3,4-dichlorobenzylamino)-5,6,7,8-tetrahydrobenzo[4,5]-thieno[2,3-d]pyrimidin-2-ylmethoxy]acetate, butyl [4-(4-chlorobenzylamino)-5,6,7,8-tetrahydrobenzo[4,5]thieno-[2,3-d]pyrimidin-2-ylmethoxy]acetate, butyl [4-(4-methylbenzylamino)-5,6,7,8-tetrahydrobenzo[4,5]thieno-[2,3-d]pyrimidin-2-ylmethoxy]acetate, butyl [4-(4-fluorobenzylamino)-5,6,7,8-tetrahydrobenzo[4,5]thieno-[2,3-d]pyrimidin-2-ylmethoxy]acetate, butyl (4-benzylamino-5,6,7,8-tetrahydrobenzo[4,5]thieno[2,3-d]-pyrimidin-2-ylmethoxy)acetate, butyl [4-(3-chloro-4-nitrobenzylamino)-5,6,7,8-tetrahydrobenzo[4,5]-thieno[2,3-d]pyrimidin-2-ylmethoxylacetate, butyl [4-(2,4-dichlorobenzylamino)-5,6,7,8-tetrahydrobenzo[4,5]-thieno[2,3-d]pyrimidin-2-ylmethoxy]acetate, butyl [4-(2-chloro-4-fluorobenzylamino)-5,6,7,8-tetrahydrobenzo[4,5]-thieno[2,3-d]pyrimidin-2-ylmethoxy]acetate, butyl [4-(3-fluorobenzylamino)-5,6,7,8-tetrahydrobenzo[4,5]thieno-[2,3-d]pyrimidin-2-ylmethoxy]acetate, butyl [4-(2-methoxybenzylamino)-5,6,7,8-tetrahydrobenzo[4,5]thieno-[2,3-d]pyrimidin-2-ylmethoxy]acetate, butyl [4-(2-chlorobenzylamino)-5,6,7,8-tetrahydrobenzo[4,5]thieno-[2,3-d]pyrimidin-2-ylmethoxy]acetate, butyl {4-[3,5-di(trifluoromethoxy)benzylamino]-5,6,7,8-tetrahydrobenzo[4,5]thieno[2,3-d]pyrimidin-2-ylmethoxy}acetate, butyl [4-(3,4-methylenedioxybenzylamino)-5,6,7,8-tetrahydrobenzo-[4,5]thieno[2,3-d]pyrimidin-2-ylethoxy]acetate, butyl [4-(3,4-dimethoxybenzylamino)-5,6,7,8-tetrahydrobenzo[4,5]-thieno[2,3-d]pyrimidin-2-ylethoxy]acetate, butyl [4-(4-methoxybenzylamino)-5,6,7,8-tetrahydrobenzo[4,5]thieno-[2,3-d]pyrimidin-2-ylethoxy]acetate, butyl [4-(3,4-dichlorobenzylamino)-5,6,7,8-tetrahydrobenzo[4,5]-thieno[2,3-d]pyrimidin-2-ylethoxy]acetate, butyl [4-(4-chlorobenzylamino)-5,6,7,8-tetrahydrobenzo[4,5]thieno-(2,3-d]pyrimidin-2-ylethoxy]acetate, butyl [4-(4-methylbenzylamino)-5,6,7,8-tetrahydrobenzo[4,5]thieno-[2,3-d]pyrimidin-2-ylethoxy]acetate, butyl [4-(4-fluorobenzylamino)-5,6,7,8-tetrahydrobenzo[4,5]thieno-[2,3-d]pyrimidin-2-ylethoxy]acetate, butyl (4-benzylamino-5,6,7,8-tetrahydrobenzo[4,5]thieno[2,3-d]-pyrimidin-2-ylethoxy)acetate, butyl [4-(3-chloro-4-nitrobenzylamino)-5,6,7,8-tetrahydrobenzo[4,5]-thieno[2,3-d]pyrimidin-2-ylethoxy]acetate, butyl [4-(2,4-dichlorobenzylamino)-5,6,7,8-tetrahydrobenzo[4,5-thieno[2,3-d]pyrimidin-2-ylethoxy]acetate, butyl [4-(2-chloro-4-fluorobenzylamino)-5,6,7,8-tetrahydrobenzo[4,5]-thieno[2,3-d]pyrimidin-2-ylethoxy]acetate, butyl [4-(3-fluorobenzylamino)-5,6,7,8-tetrahydrobenzo[4,5]thieno-[2,3-d]pyrimidin-2-ylethoxy]acetate, butyl [4-(2-methoxybenzylamino)-5,6,7,8-tetrahydrobenzo[4,5]thieno-[2,3-d]pyrimidin-2-ylethoxy]acetate, butyl [4-(2-chlorobenzylamino)-5,6,7,8-tetrahydrobenzo[4,5]thieno-[2,3-d]pyrimidin-2-ylethoxy]acetate, butyl {4-[3,5-di(trifluoromethoxy)benzylamino]-5,6,7,8-tetrahydrobenzo[4,5]thieno[2,3-d]pyrimidin-2-ylethoxy}acetate.

EXAMPLE 4

Reaction of "AB" with ethyl thioglycolate analogously to Example 1 gives the compound ethyl (4-oxo-3,4,5,6,7,8-hexahydrobenzo[4,5]thieno[2,3-d]-pyrimidin-2-ylmethylsulfanyl)acetate ("AF"), m.p. 172°.

A mixture of 4.0 g of "AF", 50 ml of phosphoryl chloride and 1 ml of N-ethyldiisopropylamine is stirred at 90° for 2 hours. After removal of the phosphoryl chloride, the mixture is subjected to conventional work-up, giving 2.5 g of ethyl (4-chloro-5,6,7,8-tetrahydrobenzo[4,5]thieno(2,3-d]-pyrimidin-2-ylmethylsulfanyl)acetate ("AG").

The following benzylamine derivatives are obtained from "AG" analogously to Example 3 ethyl [4-(3-chloro-4-methoxybenzylamino)-5,6,7,8-tetrahydrobenzo-[4,5]thieno[2,3-d]pyrimidin-2-ylmethylsulfanyl]acetate, m.p. 98–99°;

ethyl [4-(3,4-methylenedioxybenzylamino)-5,6,7,8-tetrahydrobenzo-[4,5]thieno[2,3-d]pyrimidin-2-ylmethylsulfanyl]acetate, ethyl [4-(3,4-dimethoxybenzylamino)-5,6,7,8-tetrahydrobenzo[4,5]-thieno-2,3-d]pyrimidin-2-ylmethylsulfanyl]acetate, ethyl [4-(4-methoxybenzylamino)-5,6,7,8-tetrahydrobenzo[4,5]thieno-[2,3-d]pyrimidin-2-ylmethylsulfanyl]acetate, ethyl [4-(3,4-dichlorobenzylamino)-5,6,7,8-tetrahydrobenzo[4,5]-thieno[2,3-d]pyrimidin-2-ylmethylsulfanyl]acetate, ethyl [4-(4-chlorobenzylamino)-5,6,7,8-tetrahydrobenzo[4,5]thieno-[2,3-d]pyrimidin-2-ylmethylsulfanyl]acetate, ethyl [4-(4-methylbenzylamino)-5,6,7,8-tetrahydrobenzo[4,5]thieno-[2,3-d]pyrimidin-2-ylmethylsulfanyl]acetate, ethyl [4-(4-fluorobenzylamino)-5,6,7,8-tetrahydrobenzo[4,5]thieno-[2,3-d]pyrimidin-2-ylmethylsulfanyl]acetate, ethyl (4-benzylamino-5,6,7,8-tetrahydrobenzo[4,5]thieno[2,3-d]-pyrimidin-2-ylmethylsulfanyl)acetate, ethyl [4-(3-chloro-4-nitrobenzylamino)-5,6,7,8-tetrahydrobenzo[4,5]-thieno[2,3-d]pyrimidin-2-ylmethylsulfanyl]acetate, ethyl [4-(2,4-d]chlorobenzylamino)-5,6,7,8-tetrahydrobenzo[4,5]-thieno[2,3-d]pyrimidin-2-ylmethylsulfanyl]acetate, ethyl [4-(2-chloro-4-fluorobenzylamino)-5,6,7,8-tetrahydrobenzo[4,5]-thieno[2,3-d]pyrimidin-2-ylmethylsulfanyl]acetate, ethyl [4-(3-fluorobenzylamino)-5,6,7,8-tetrahydrobenzo[4,5]thieno-[2,3-d]pyrimidin-2-ylmethylsulfanyl]acetate, ethyl [4-(2-methoxybenzylamino)-5,6,7,8-tetrahydrobenzo[4,5]thieno-[2,3-d]pyrimidin-2-ylmethylsulfanyl]acetate, ethyl [4-(2-chlorobenzylamino)-5,6,7,8-tetrahydrobenzo[4,5]thieno-[2,3-d]pyrimidin-2-ylmethylsulfanyl]acetate, ethyl {4-[3,5-di(trifluoromethoxy)benzylamino]-5,6,7,8-tetrahydrobenzo[4,5]thieno[2,3-d]pyrimidin-2-ylmethylsulfanyl}acetate.

EXAMPLE 5

1.1 g of hydrogen peroxide (30%) are added to a solution of 2.0 g of ethyl [4-(3-chloro-4-methoxybenzylamino)-5,6,7,8-tetrahydrobenzo[4,5]thieno-[2,3-d]pyrimidin-2-ylmethylsulfanyl]acetate in 50 ml of glacial acetic acid, and the mixture is stirred at room temperature for 3 hours.

The mixture is subjected to conventional work-up, giving 1.7 g of ethyl [4-(3-chloro-4-methoxybenzylamino)-5,6,7,8-tetrahydrobenzo[4,5]thieno-[2,3-d]pyrimidin-2-ylmethylsulfanyl]acetate, m.p. 158–160°.

The following compounds are obtained analogously from the sulfanyl derivatives obtained in Example 4 ethyl [4-(3,4-methylenedioxybenzylamino)-5,6,7,8-tetrahydrobenzo-[4,5]thieno[2,3-d]pyrimidin-2-ylmethylsulfinyl]acetate, ethyl [4-(3,4-dimethoxybenzylamino)-5,6,7,8-tetrahydrobenzo[4,5]-thieno[2,3-d]pyrimidin-2-ylmethylsulfinyl]acetate, ethyl [4-(4-methoxybenzylamino)-5,6,7,8-tetrahydrobenzo[4,5]thieno-[2,3-d]pyrimidin-2-ylmethylsulfinyl]acetate, ethyl [4-(3,4-dichlorobenzylamino)-5,6,7,8-tetrahydrobenzo[4,5]-thieno[2,3-d]pyrimidin-2-ylmethylsulfinyl]acetate, ethyl [4-(4-chlorobenzylamino)-5,6,7,8-tetrahydrobenzo[4,5]thieno-[2,3-d]pyrimidin-2-ylmethylsulfinyl]acetate, ethyl [4-(4-methylbenzylamino)-5,6,7,8-tetrahydrobenzo[4,5]thieno-[2,3-d]pyrimidin-2-ylmethylsulfinyl]acetate, ethyl [4-(4-fluorobenzylamino)-5,6,7,8-tetrahydrobenzo[4,5]thieno-[2,3-d]pyrimidin-2-ylmethylsulfinyl]acetate, ethyl (4-benzylamino-5,6,7,8-tetrahydrobenzo[4,5]thieno[2,3-d]-pyrimidin-2-ylmethylsulfinyl)acetate, ethyl [4-(3-chloro-4-nitrobenzylamino)-5,6,7,8-tetrahydrobenzo[4,5]-thieno[2,3-d]pyrimidin-2-ylmethylsulfinyl]acetate, ethyl (4-(2,4-dichlorobenzylamino)-5,6,7,8-tetrahydrobenzo[4,5]-thieno[2,3-d]pyrimidin-2-ylmethylsulfinyl]acetate, ethyl [4-(2-chloro-4-fluorobenzylamino)-5,6,7,8-tetrahydrobenzo[4,5]-thieno[2,3-d]pyrimidin-2-ylmethylsulfinyl]acetate, ethyl [4-(3-fluorobenzylamino)-5,6,7,8-tetrahydrobenzo[4,5]thieno-[2,3-d]pyrimidin-2-ylmethylsulfinyl]acetate, ethyl [4-(2-methoxybenzylamino)-5,6,7,8-tetrahydrobenzo[4,5]thieno-[2,3-d]pyrimidin-2-ylmethylsulfinyl]acetate, ethyl [4-(2-chlorobenzylamino)-5,6,7,8-tetrahydrobenzo[4,5]thieno-[2,3-d]pyrimidin-2-ylmethylsulfinyl]acetate, ethyl {4-[3,5-di(trifluoromethoxy)benzylamino]-5,6,7,8-tetrahydrobenzo[4,5]thieno[2,3-d]pyrimidin-2-ylmethylsulfinyl}acetate.

EXAMPLE 6

A solution of 1.8 g of butyl [4-(3-chloro-4-methoxybenzylamino)-5,6,7,8-tetrahydrobenzo[4,5]thieno[2,3-d]pyrimidin-2-ylmethoxy]acetate in 60 ml of ethylene glycol monoethyl ether and 20 ml of 2M NaOH is stirred in a steam bath for 30 minutes.

The mixture is subjected to conventional work-up, giving 1.7 g of [4-(3-chloro-4-methoxybenzylamino)-5,6,7,8-tetrahydrobenzo[4,5]thieno-[2,3-d]pyrimidin-2-ylmethoxy] acetic acid, m.p. 136–137°.

The resultant compound is dissolved at elevated temperature is 20 ml of isopropanol and 0.3 g of ethanolamine and cooled, and ether is added. The precipitated crystals are separated off, giving 1.7 g of [4-(3-chloro-4-methoxybenzylamino)-5,6,7,8-tetrahydrobenzo[4,5]thieno[2,3-d]pyrimidin-2-ylmethoxy]acetic acid, ethanolamine salt, m.p. 148–149°.

The following carboxylic acid derivatives are obtained analogously from the esters obtained in Example 3

[4-(3,4-methylenedioxybenzylamino)-5,6,7,8-tetrahydrobenzo[4,5]-thieno[2,3-d]pyrimidin-2-ylmethoxy]acetic acid,

[4-(3,4-dimethoxybenzylamino)-5,6,7,8-tetrahydrobenzo[4,5]thieno-[2,3-d]pyrimidin-2-ylmethoxy]acetic acid,

[4-(4-methoxybenzylamino)-5,6,7,8-tetrahydrobenzo[4,5]thieno-[2,3-d]pyrimidin-2-ylmethoxy]acetic acid,

[4-(3,4-dichlorobenzylamino)-5,6,7,8-tetrahydrobenzo[4,5]thieno-[2,3-d]pyrimidin-2-ylmethoxy]acetic acid,

[4-(4-chlorobenzylamino)-5,6,7,8-tetrahydrobenzo[4,5]thieno[2,3-d]-pyrimidin-2-ylmethoxy]acetic acid,

[4-(4-methylbenzylamino)-5,6,7,8-tetrahydrobenzo[4,5]thieno[2,3-d]-pyrimidin-2-ylmethoxy]acetic acid,

[4-(4-fluorobenzylamino)-5,6,7,8-tetrahydrobenzo[4,5]thieno[2,3-d]-pyrimidin-2-ylmethoxy]acetic acid, (4-benzylamino-5,6,7,8-tetrahydrobenzo[4,5]thieno[2,3-d]pyrimidin-2-ylmethoxy)acetic acid,

[4-(3-chloro-4-nitrobenzylamino)-5,6,7,8-tetrahydrobenzo[4,5]thieno-[2,3-d]pyrimidin-2-ylmethoxy]acetic acid,

[4-(2,4-dichlorobenzylamino)-5,6,7,8-tetrahydrobenzo[4,5]thieno-[2,3-d]pyrimidin-2-ylmethoxy]acetic acid,

[4-(2-chloro-4-fluorobenzylamino)-5,6,7,8-tetrahydrobenzo[4,5]-thieno[2,3-d]pyrimidin-2-ylmethoxy]acetic acid,

[4-(3-fluorobenzylamino)-5,6,7,8-tetrahydrobenzo[4,5]thieno[2,3-d]-pyrimidin-2-ylmethoxy]acetic acid,

[4-(2-methoxybenzylamino)-5,6,7,8-tetrahydrobenzo[4,5]thieno-[2,3-d]pyrimidin-2-ylmethoxy]acetic acid,

[4-(2-chlorobenzylamino)-5,6,7,8-tetrahydrobenzo[4,5]thieno[2,3-d]-pyrimidin-2-ylmethoxy]acetic acid, {4-[3,5-di(trifluoromethoxy)benzylamino]-5,6,7,8-tetrahydrobenzo-[4,5]thieno[2,3-d]pyrimidin-2-ylmethoxy}acetic acid,

[4-(3-chloro-4-methoxybenzylamino)-5,6,7,8-tetrahydrobenzo[4,5]-thieno[2,3-d]pyrimidin-2-ylethoxy]acetic acid, ethanolamine salt, 139–140°;

[4-(3,4-methylenedioxybenzylamino)-5,6,7,8-tetrahydrobenzo[4,5]-thieno[2,3-d]pyrimidin-2-ylethoxy]acetic acid,

[4-(3,4-dimethoxybenzylamino)-5,6,7,8-tetrahydrobenzo[4,5]thieno-[2,3-d]pyrimidin-2-ylethoxy]acetic acid,

[4-(4-methoxybenzylamino)-5,6,7,8-tetrahydrobenzo[4,5]thieno-[2,3-d]pyrimidin-2-ylethoxy]acetic acid,

[4-(3,4-dichlorobenzylamino)-5,6,7,8-tetrahydrobenzo[4,5]thieno-[2,3-d]pyrimidin-2-ylethoxy]acetic acid,

[4-(4-chlorobenzylamino)-5,6,7,8-tetrahydrobenzo[4,5]thieno[2,3-d]-pyrimidin-2-ylethoxy]acetic acid,

[4-(4-methylbenzylamino)-5,6,7,8-tetrahydrobenzo[4,5]thieno[2,3-d]-pyrimidin-2-ylethoxy]acetic acid,

[4-(4-fluorobenzylamino)-5,6,7,8-tetrahydrobenzo[4,5]thieno[2,3-d]-pyrimidin-2-ylethoxy]acetic acid, (4-benzylamino-5,6,7,8-tetrahydrobenzo[4,5]thieno[2,3-d]pyrimidin-2-ylethoxy)acetic acid,

[4-(3-chloro-4-nitrobenzylamino)-5,6,7,8-tetrahydrobenzo[4,5]thieno-[2,3-d]pyrimidin-2-ylethoxy]acetic acid,

[4-(2,4-dichlorobenzylamino)-5,6,7,8-tetrahydrobenzo[4,5]thieno-[2,3-d]pyrimidin-2-ylethoxy]acetic acid,

[4-(2-chloro-4-fluorobenzylamino)-5,6,7,8-tetrahydrobenzo[4,5]-thieno[2,3-d]pyrimidin-2-ylethoxy]acetic acid,

[4-(3-fluorobenzylamino)-5,6,7,8-tetrahydrobenzo[4,5]thieno[2,3-d]-pyrimidin-2-ylethoxy]acetic acid,

[4-(2-methoxybenzylamino)-5,6,7,8-tetrahydrobenzo[4,5]thieno-[2,3-d]pyrimidin-2-ylethoxy]acetic acid,

[4-(2-chlorobenzylamino)-5,6,7,8-tetrahydrobenzo[4,5]thieno[2,3-d]-pyrimidin-2-ylethoxy]acetic acid, {4-[3,5-di(trifluoromethoxy)benzylamino]-5,6,7,8-tetrahydrobenzo-[4,5]thieno[2,3-d]pyrimidin-2-ylethoxy}acetic acid.

EXAMPLE 7

The following carboxylic acid derivatives are obtained analogously to Example 6 by ester cleavage from the ethyl ester derivatives obtained in Examples 4 and 5 using NaOH in methanol

[4-(3-chloro-4-methoxybenzylamino)-5,6,7,8-tetrahydrobenzo[4,5]-thieno[2,3-d]pyrimidin-2-ylmethylsulfanyl]acetic acid, ethanolamine salt, m.p. 161–162°;

[4-(3,4-methylenedioxybenzylamino)-5,6,7,8-tetrahydrobenzo[4,5]-thieno[2,3-d]pyrimidin-2-ylmethylsulfanyl]acetic acid,

[4-(3,4-dimethoxybenzylamino)-5,6,7,8-tetrahydrobenzo[4,5]thieno-[2,3-d]pyrimidin-2-ylmethylsulfanyl]acetic acid,

[4-(4-methoxybenzylamino)-5,6,7,8-tetrahydrobenzo[4,5]thieno-[2,3-d]pyrimidin-2-ylmethylsulfanyl]acetic acid,

[4-(3,4-dichlorobenzylamino)-5,6,7,8-tetrahydrobenzo[4,5]thieno-[2,3-d]pyrimidin-2-ylmethylsulfanyl]acetic acid,

[4-(4-chlorobenzylamino)-5,6,7,8-tetrahydrobenzo[4,5]thieno(2,3-d]-pyrimidin-2-ylmethylsulfanyl]acetic acid,

[4-(4-methylbenzylamino)-5,6,7,8-tetrahydrobenzo[4,5]thieno[2,3-d]-pyrimidin-2-ylmethylsulfanyl]acetic acid,

[4-(4-fluorobenzylamino)-5,6,7,8-tetrahydrobenzo[4,5]thieno[2,3-d]-pyrimidin-2-ylmethylsulfanyl]acetic acid, (4-benzylamino-5,6,7,8-tetrahydrobenzo[4,5]thieno[2,3-d]pyrimidin-2-ylmethylsulfanyl)acetic acid,

[4-(3-chloro-4-nitrobenzylamino)-5,6,7,8-tetrahydrobenzo[4,5]thieno-[2,3-d]pyrimidin-2-ylmethylsulfanyl]acetic acid,

[4-(2,4-dichlorobenzylamino)-5,6,7,8-tetrahydrobenzo[4,5]thieno-[2,3-d]pyrimidin-2-ylmethylsulfanyl]acetic acid,

[4-(2-chloro-4-fluorobenzylamino)-5,6,7,8-tetrahydrobenzo[4,5]-thieno[2,3-d]pyrimidin-2-ylmethylsulfanyl]acetic acid,

[4-(3-fluorobenzylamino)-5,6,7,8-tetrahydrobenzo[4,5]thieno[2,3-d]-pyrimidin-2-ylmethylsulfanyl]acetic acid,

[4-(2-methoxybenzylamino)-5,6,7,8-tetrahydrobenzo[4,5]thieno-[2,3-d]pyrimidin-2-ylmethylsulfanyl]acetic acid,

[4-(2-chlorobenzylamino)-5,6,7,8-tetrahydrobenzo[4,5]thieno[2,3-d]-pyrimidin-2-ylmethylsulfanyl]acetic acid, {4-[3,5-di(trifluoromethoxy)benzylamino]-5,6,7,8-tetrahydrobenzo-[4,5]thieno[2,3-d]pyrimidin-2-ylmethylsulfanyl}acetic acid,

[4-(3-chloro-4-methoxybenzylamino)-5,6,7,8-tetrahydrobenzo[4,5]-thieno(2,3-d]pyrimidin-2-ylmethylsulfinyl]acetic acid, ethanolamine salt, amorphous,

[4-(3,4-methylenedioxybenzylamino)-5,6,7,8-tetrahydrobenzo[4,5]-thieno[2,3-d]pyrimidin-2-ylmethylsulfinyl]acetic acid,

[4-(3,4-dimethoxybenzylamino)-5,6,7,8-tetrahydrobenzo[4,5]thieno-[2,3-d]pyrimidin-2-ylmethylsulfinyl]acetic acid,

[4-(4-methoxybenzylamino)-5,6,7,8-tetrahydrobenzo[4,5]thieno-[2,3-d]pyrimidin-2-ylmethylsulfinyl]acetic acid,

[4-(3,4-dichlorobenzylamino)-5,6,7,8-tetrahydrobenzo[4,5]thieno-[2,3-d]pyrimidin-2-ylmethylsulfinyl]acetic acid,

[4-(4-chlorobenzylamino)-5,6,7,8-tetrahydrobenzo[4,5]thieno[2,3-d]-pyrimidin-2-ylmethylsulfinyl]acetic acid,

[4-(4-methylbenzylamino)-5,6,7,8-tetrahydrobenzo[4,5]thieno[2,3-d]-pyrimidin-2-ylmethylsulfinyl]acetic acid,

[4-(4-fluorobenzylamino)-5,6,7,8-tetrahydrobenzo[4,5]thieno[2,3-d]-pyrimidin-2-ylmethylsulfinyl]acetic acid, (4-benzylamino-5,6,7,8-tetrahydrobenzo[4,5]thieno[2,3-d]pyrimidin-2-ylmethylsulfinyl)acetic acid,

[4-(3-chloro-4-nitrobenzylamino)-5,6,7,8-tetrahydrobenzo[4,5]thieno-[2,3-d]pyrimidin-2-ylmethylsulfinyl]acetic acid,

[4-(2,4-dichlorobenzylamino)-5,6,7,8-tetrahydrobenzo[4,5]thieno-[2,3-d]pyrimidin-2-ylmethylsulfinyl]acetic acid,

[4-(2-chloro-4-fluorobenzylamino)-5,6,7,8-tetrahydrobenzo[4,5]-thieno[2,3-d]pyrimidin-2-ylmethylsulfinyl]acetic acid,

[4-(3-fluorobenzylamino)-5,6,7,8-tetrahydrobenzo[4,5]thieno[2,3-d]-pyrimidin-2-ylmethylsulfinyl]acetic acid,

[4-(2-methoxybenzylamino)-5,6,7,8-tetrahydrobenzo[4,5]thieno-[2,3-d]pyrimidin-2-ylmethylsulfinyl]acetic acid,

[4-(2-chlorobenzylamino)-5,6,7,8-tetrahydrobenzo[4,5]thieno[2,3-d]-pyrimidin-2-ylmethylsulfinyl]acetic acid, {4-[3,5-di(trifluoromethoxy)benzylamino]-5,6,7,8-tetrahydrobenzo-[4,5]thieno[2,3-d]pyrimidin-2-ylmethylsulfinyl}acetic acid.

The examples below relate to pharmaceutical preparations,

EXAMPLE A

Injection Vials

A solution of 100 g of an active ingredient of the formula I and 5 g of disodium hydrogen phosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of an active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of an active ingredient of the formula I are introduced into hard gelatine capsules in a conventional manner in such a way that each capsule contains 20 mg of the active ingredient.

EXAMPLE H

Ampoules

A solution of 1 kg of an active ingredient of the formula I in 60 l of bidistilled water is sterile filtered transferred into ampoules, lyophilised under sterile conditions and sealed under sterile conditions. Each ampoule contains 10 mg of active ingredient.

EXAMPLE I

Inhalation Spray 14 g of an active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

What is claimed is:

1. A compound of the formula I

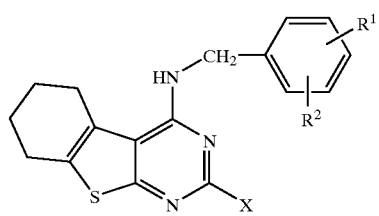

(I)

in which
$R^1$ and $R^2$ are each, independently of one another, H, A, OH, OA, $NO_2$ or Hal,
$R^1$ and $R^2$ together are alternatively alkylene having 3–5 carbon atoms, $-O-CH_2-CH_2-$, $-CH_2-O-CH_2-$, $-O-CH_2-O-$ or $-O-CH_2-CH_2-O-$,
X is mono-$R^5$-substituted $R^3$ or $R^4$,
$R^3$ is linear or branched alkylene having 1–10 carbon atoms, in which one or two $CH_2$ groups are optionally replaced by $-CH=CH-$ groups, O, NH or NA,
$R^4$ is cycloalkyl or cycloalkylalkylene having 5–12 carbon atoms,
$R^5$ is $O(CH_2)_nCOOH$, $O(CH_2)_nCOOA$, $O(CH_2)_nCONH_2$, $O(CH_2)_nCONHA$, $O(CH_2)_nCONA_2$, $O(CH_2)_nCN$, $S(O)_m(CH_2)_nCOOH$, $S(O)_m(CH_2)_nCOOA$, $S(O)_m(CH_2)_nCONH_2$, $S(O)_m(CH_2)_nCONHA$, $S(O)_m(CH_2)_nCONA_2$ or $S(O)_m(CH_2)_nCN$
m is 0, 1 or 2,
n is 1 or 2,
A is alkyl having 1 to 6 carbon atoms, and
Hal is F, Cl, Br or I,
or a physiologically acceptable salt thereof.

2. A compound according to claim 1,
in which
X is $R^3$ which is substituted by $O(CH_2)_nCOOH$, $O(CH_2)_nCOOA$, $O(CH_2)_nCONH_2$, $O(CH_2)_nCONHA$, $O(CH_2)_n CONA_2$, $O(CH_2)_nCN$, $S(O)_m(CH_2)_nCOOH$, $S(O)_m(CH_2)_nCOOA$, $S(O)_m(CH_2)_nCONH_2$, $S(O)_m(CH_2)_n CONHA$, $S(O)_m(CH_2)_nCONA_2$ or $S(O)_m(CH_2)_nCN$,
or a physiologically acceptable salt thereof.

3. A compound according to claim 1,
in which
$R^1$ and $R^2$ are each, independently of one another, Hal, OH or OA, and
X is $R^3$ which is substituted by $O(CH_2)_nCOOH$, $O(CH_2)_n COOA$, $S(O)_m(CH_2)_nCOOH$ or $S(O)_m(CH_2)_nCOOA$,
or a physiologically acceptable salt thereof.

4. A compound according to claim 1,
in which
$R^1$ and $R^2$ are each, independently of one another, Hal, OH or OA,
X is $R^3$ which is substituted by $O(CH_2)_nCOOH$, $O(CH_2)_n COOA$, $S(O)_m(CH_2)_nCOOH$ or $S(O)_m(CH_2)_nCOOA$, and
$R^3$ is methylene, ethylene or propylene,
or a physiologically acceptable salt thereof.

5. A compound according to claim 1,
in which
$R^1$ and $R^2$ are each, independently of one another, Hal, OH or OA,
$R^1$ and $R^2$ together are alkylene having 3–5 carbon atoms, $-O-CH_2-CH_2-$, $-O-CH_2-O-$ or $-O-CH_2-CH_2-O$,
X is $R^3$ which is substituted by $O(CH_2)_nCOOH$, $O(CH_2)_n COOA$, $S(O)_m(CH_2)_nCOOH$ or $S(O)_m(CH_2)_nCOOA$, and
$R^3$ is methylene, ethylene or propylene,
or a physiologically acceptable salt thereof.

6. A Compound according to claim 1,
in which
$R^1$ and $R^2$ are each, independently of one another, H, Hal, A, $NO_2$, OH or OA,
$R^1$ and $R^2$ together are alkylene having 3–5 carbon atoms, $-O-CH_2-CH_2-$, $-O-CH_2-O-$ or $-O-CH_2-CH_2-O$,
X is $R^3$ which is substituted by $O(CH_2)_nCOOH$, $O(CH_2)_n COOA$, $S(O)_m(CH_2)_nCOOH$ or $S(O)_m(CH_2)_nCOOA$,
$R^3$ is methylene, ethylene or propylene, and
A is alkyl having 1–6 carbon atoms or $CF_3$,
or a physiologically acceptable salt thereof.

7. A Compound according to claim 1,
in which
$R^1$ and $R^2$ are each, independently of one another, H, Hal, A, $NO_2$, OH or OA,
$R^1$ and $R^2$ together are $-O-CH_2-O-$ or $-O-CH_2-CH_2-O-$,
X is $R^3$ which is substituted by $O(CH_2)_nCOOH$, $O(CH_2)_n COOA$, $S(O)_m(CH_2)_nCOOH$ or $S(O)_m(CH_2)_nCOOA$,
$R^3$ is methylene, ethylene or propylene, and
A is alkyl having 1–6 carbon atoms or $CF_3$,
or a physiologically acceptable salt thereof.

8. A Compound according to claim 1,
which is selected from the group consisting of:
(a) 2-[4-(3-chloro-4-methoxybenzylamino)-5,6,7,8-tetrahydro[4,5]-benzothieno[2,3-d]pyrimidin-2-ylmethoxy]acetic acid;
(b) 2-[4-(3-chloro-4-methoxybenzylamino)-5,6,7,8-tetrahydro[4,5]-benzothieno[2,3-d]pyrimidin-2-ylmethylsulfanyl]acetic acid;

(c) 2-[4-(3-chloro-4-methoxybenzylamino)-5,6,7,8-tetrahydro[4,5]-benzothieno[2,3-d]pyrimidin-2-ylmethylsulfinyl]acetic acid;

(d) 2-[4-(3-chloro-4-methoxybenzylamino)-5,6,7,8-tetrahydro[4,5]-benzothieno[2,3-d]pyrimidin-2-ylethoxy]acetic acid;

and physiologically acceptable salts thereof.

9. A process for the preparation of compounds of a compound of the formula I according to claim 1 or a salt thereof, which comprises:

a) reacting a compound of the formula II

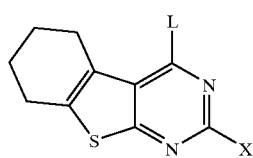

in which

X is as defined above, and L is Cl, Br, OH, SCH₃ or a reactive esterified OH group, with a compound of the formula III

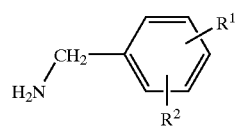

in which

R¹ and R² are as defined above, b) optionally, converting a radical X in a compound of the resulting formula I into another radical X by hydrolysing an ester group to a COOH group or converting a COOH group into an amide or into a cyano group, and c) optionally, converting a resulting compound of the formula I into one of its salts.

10. A pharmaceutical composition comprising at least one compound according to claim 1, or a physiologically acceptable salt thereof, and at least one pharmaceutically acceptable excipient.

11. A method for treating cardiac insufficiency in a patient, which comprises administering to the patient a compound according to claim 1 or a physiologically acceptable salt thereof.

12. The method of claim 11, wherein the cardiac insufficiency is angina, high blood pressure, high pulmonary pressure, congestive heart failure, atherosclerosis, a condition of reduced passage through the heart vessels, a peripheral vascular disease, or stroke.

13. A method for treating bronchitis, allergic asthma, chronic asthma, allergic rhinitis, glaucoma, irritable bowel syndrome, a tumor, renal insufficiency, liver cirrhosis or a female sexual disorder, which comprises administering to the patient a compound according to claim 1 or a physiologically acceptable salt thereof.

14. A method for the therapy of impotence, which comprises administering to the patient a compound according to claim 1 or a physiologically acceptable salt thereof.

15. The method of claim 11, wherein the compound is administered in a daily dose of from 0.02 to 10 mg/kg of the patient body weight.

16. The method of claim 12, wherein the compound is administered in a daily dose of from 0.02 to 10 mg/kg of the patient body weight.

17. The method of claim 11, wherein the compound is administered orally.

18. The method of claim 12, wherein the compound is administered orally.

19. The method of claim 13, wherein the compound is administered in a daily dose of from 0.02 to 10 mg/kg of the patient body weight.

20. The method of claim 14, wherein the compound is administered in a daily dose of from 0.02 to 10 mg/kg of the patient body weight.

* * * * *